United States Patent [19]

Dwulet et al.

[11] Patent Number: 5,753,485

[45] Date of Patent: May 19, 1998

[54] PURIFIED MIXTURE OF COLLAGENASE I, COLLAGENASE II AND TWO OTHER PROTEASES

[75] Inventors: Francis E. Dwulet, Greenwood; Bernice B. Ellis, Greenfield; John F. Gill; Linda B. Jacobsen, both of Indianapolis; Marilyn E. Smith, McCordsville; David G. Waters, Indianapolis, all of Ind.

[73] Assignee: Boehringer Mannheim Corporation, Indianapolis, Ind.

[21] Appl. No.: 590,957

[22] Filed: Jan. 24, 1996

Related U.S. Application Data

[63] Continuation of Ser. No. 265,292, Jun. 24, 1994, abandoned.

[51] Int. Cl.$^6$ .................................. C12N 9/52; C12N 9/50
[52] U.S. Cl. .................................. 435/220; 435/219
[58] Field of Search ........................ 435/220, 183, 435/219

[56] References Cited

U.S. PATENT DOCUMENTS

| | | | |
|---|---|---|---|
| 3,201,325 | 8/1965 | Barton | 195/66 |
| 3,705,083 | 12/1972 | Chiulli et al. | 195/62 |
| 3,821,364 | 6/1974 | Chiulli et al. | 424/94 |
| 4,256,836 | 3/1981 | Isowa et al. | 435/70 |
| 4,431,544 | 2/1984 | Atkinson | 210/635 |
| 4,431,546 | 2/1984 | Hughes | 210/656 |
| 4,732,758 | 3/1988 | Hurion | 424/94.2 |
| 4,797,213 | 1/1989 | Parisius et al. | 210/651 |
| 4,868,121 | 9/1989 | Scharp et al. | 435/268 |
| 4,873,359 | 10/1989 | Chmurny et al. | 560/40 |
| 4,946,792 | 8/1990 | O'Leary | 435/268 |
| 5,079,160 | 1/1992 | Lacy et al. | 435/240.2 |
| 5,116,615 | 5/1992 | Gokcen et al. | 424/94.2 |
| 5,120,656 | 6/1992 | O'Leary et al. | 435/268 |
| 5,173,295 | 12/1992 | Wehling | 424/94.67 |
| 5,177,017 | 1/1993 | Lin et al. | 435/252.33 |
| 5,273,904 | 12/1993 | Langley | 435/287 |
| 5,322,790 | 6/1994 | Scharp | 435/268 |
| 5,332,503 | 7/1994 | Lee et al. | 210/635 |
| 5,422,261 | 6/1995 | Lee et al. | 435/219 |

FOREIGN PATENT DOCUMENTS

| | | | |
|---|---|---|---|
| 0 191 613 A2 | 8/1986 | European Pat. Off. | C12N 5/00 |
| WO 91/14447 | 10/1991 | WIPO | A61K 37/54 |
| WO 94/04666 | 3/1994 | WIPO . | |

OTHER PUBLICATIONS

Suggs et al., J. Vasc. Surg. 15(1):205–213 (1992).
Maruyama et al., J. Pharm. Methods 18:151–161 (1987).
Patel, *Biotechnology: Applications & Research* Edited by Cheremisinoff et al., 1985, pp. 534–562, Published by Technomic Publishing Company, Inc., Lancaster, Penn.
Bond et al., "Purification and Separation of Individual Collagenases of *Clostridium histolyticum* Using Red Dye Ligand Chromatography", 1984, pp. 3077–3085, *Biochemistry* vol. 23 No. 13.

Bond et al., "Characterization of the Individual Collagenases from *Clostridium histolyticum*", 1984, pp. 3085–3091, *Biochemistry* vol. 23 No. 13.
Worthington, "Worthington Enzyme Manual–enzymes and related biochemicals", 1988, pp. 93–101, Worthington Biochemical Corporation.
Kono, "Purification and Partial Characterization of Collagenolytic Enzymes from *Clostridium histolyticum*", Mar. 1968, pp. 1106–1114, *Biochemistry* vol. 7 No. 3.
Kula et al., "Consecutive Use of ω–Aminoalkylagaroses. Resolution and Purification of Clostripain and Collagenase from *C. histolyticum*", 1976, pp. 389–396, *Bioch. & Bioph. Res. Comm.* vol. 69 No. 2.
Emöd et al., "Five Sepharose–Bound Ligands for the Chromatographic Purification of Clostridium Collagenase and Clostripain", 1977, pp. 51–56, *FEBS Letters* vol. 77 No. 1.
Hefley et al., "Enzymatic isolation of cells from bone: cytotoxic enzymes of bacterial collagenase", 1981, pp. C234–C238, *Am. J. Physiology* 240.
Hatton et al., "The role of proteolytic enzymes derived from crude bacterial collagenase in the liberation of hepatocytes from rat liver", 1983, pp. 311–318, *J. Biochem.* 137.
Hefley et al., "Enzymatic Isolation of Cells from Neonatal Calvaria Using Two Purified Enzymes from *Clostridium histolyticum*", 1983, pp. 227–236, *Experimental Cell Research* 149.
Hefley, "Utilization of FPLC–Purified Bacterial Collagenase from the Isolation of Cells from Bone", 1987, pp. 505–516, *Journal of Bone and Mineral Research* vol. 2 No. 7.
McShane et al., "Protease Activity in Pancreatic Islet Isolation by Enzymatic Digestion", 1989, pp. 126–128, *Diabetes* vol. 38 Suppl. 1.
Wolters et al., "An analysis of the role of collagenase and protease in the enzymatic dissociation of rat pancreas for islet isolation", 1992, pp. 735–742, *Diabetologia* 35.
Kobayashi et al., "Purification and Characterization of Myosin from Bovine Thyroid", Nov. 25, 1977, pp. 8285–8291, *The Journal of Biological Chemistry*, vol. 252, No. 22.
Silink et al., "γ–Glutamyl Hydrolase (Conjugase)", Aug. 10, 1975, pp. 5982–5994, *The Journal of Biological Chemistry*, vol. 250, No. 15.
Dean et al., "Protein Purification Using Immobilized Trizine Dyes", 1979, pp. 301–319, *Journal of Chromatography*, 165.

*Primary Examiner*—Sandra E. Saucier
*Attorney, Agent, or Firm*—Brent A. Harris; D. Michael Young; Marilyn L. Amick

[57] ABSTRACT

A purified enzyme mixture useful for isolating cells or cell clusters from tissue is disclosed. The mixture includes at least two collagenase enzymes, at least two other proteases, and additional non-protease components. The mixture is purified by removing at least some of the non-protease components. The purified mixture may then be used to isolate cells or cell clusters from tissue. Also disclosed are the essential components of the purified enzyme mixture as well as preferred ranges and ratios of these essential components for isolating cells or cell clusters from tissue. Finally, a dissociation system is disclosed that can be used with the purified enzyme mixture to dissociate tissue and recover cells or cell clusters.

21 Claims, 3 Drawing Sheets

PURIFIED MIXTURE OF COLLAGENASE I, COLLAGENASE II AND TWO OTHER PROTEASES

This application is a continuation of application Ser. No. 08/265,292, filed Jun. 24, 1994, now abandoned.

FIELD OF THE INVENTION

This invention relates to the enzymatic isolation of cells or cell clusters from tissue.

BACKGROUND OF THE INVENTION

The enzymatic isolation of cells and cell clusters from liver, pancreas, skin, cartilage, bone, neural tissue, and other organs has been accomplished and proven to be useful for various purposes including cellular characterization and implantation, e.g., isolation of islets of Langerhans (islets) from the pancreas for implantation in diabetic patients. Since collagen is a prominent structural protein within tissue, the enzyme collagenase is frequently used as a means of accomplishing the desired isolation.

Several forms of crude collagenase, e.g., crude bacterial collagenase derived from *Clostridium histolyticum*, are commercially available and have proven to be useful in isolating cells and cell clusters from tissue. These crude collagenases are actually a mixture of protease enzymes exhibiting collagenolytic and proteolytic activity and non-protease components, including fermentation by-products, fermentation media, pigment, and other enzymes (e.g. phospholipase). These non-protease components of crude collagenase are generally recognized by those skilled in the art as being inert, that is, not affecting the activity of the protease enzymes.

Unfortunately, these commercially available crude collagenases have been shown to contain varying amounts of the protease and non-protease components, thereby causing substantial variations in efficacy between lots. In addition to variability problems, use of these crude collagenases in research has resulted in poor cell integrity, low cell number, and fragmented cell clusters. These problems are significant, especially when the isolated cells or cell clusters are subsequently transplanted. For example, it has been shown that the efficacy of the transplanted islet mass, i.e. its ability to produce insulin in a host, is greatly diminished with reduced size and number.

The importance of the protease enzymes to the process of obtaining an efficacious cellular isolation, i.e. maintaining cellular integrity, isolating larger cell clusters and isolating more cells or cell clusters, has been recognized by those skilled in the art. Specifically, the presence of collagenase Class I (collagenase I) and collagenase Class II (collagenase II) enzymes and the presence of a neutral protease have been found to influence the efficacy of the cellular isolation. The protease clostripain has been reported to have a negative influence on certain cell isolations (Hefley, *J. Bone and Mineral Res.* 2:6, 1987, pp.505–516). However, while many of the problems associated with obtaining a pure cell isolation have been defined, appropriate remedies have heretofore remained undiscovered.

SUMMARY OF THE INVENTION

The present invention provides a purified enzyme mixture and a method for performing the purification. The enzyme mixture includes at least two collagenase enzymes, at least two other proteases and non-protease components, and is purified by removing at least some of the non-protease components. The removal of at least some of these non-protease components, considered by the prior art to be inert, unexpectedly results in a purified enzyme mixture that is capable of isolating cells or cell clusters from tissue with greater efficacy and efficiency than an unpurified enzyme mixture possessing the same level of enzyme activities.

DESCRIPTION OF THE INVENTION

Figure 1:
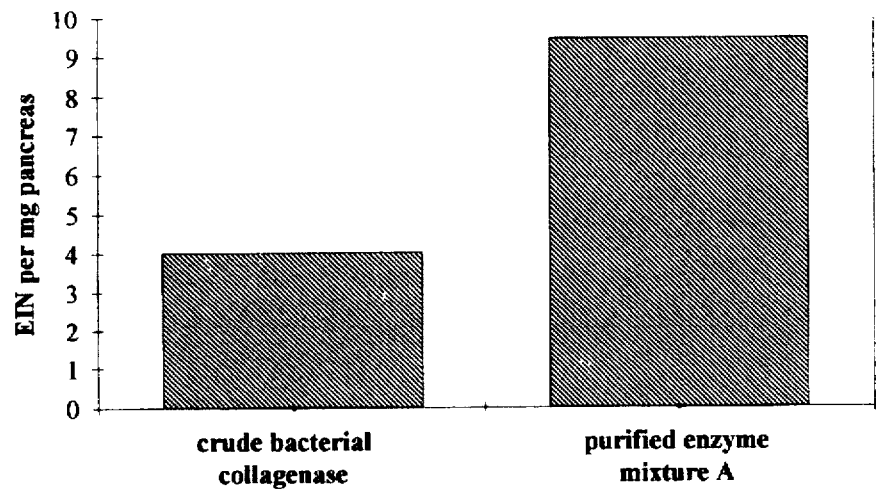
FIG. 1 shows the improvement in performance in pancreatic dissociation after dye ligand affinity chromatography.

This invention is based on the discovery that when a mixture of crude collagenase is purified by removing at least some of the non-protease components which have heretofore been considered by the prior art to be inert, an unexpected improvement in performance in tissue dissociation is seen. The purified enzyme mixture of the present invention is useful for isolating cells or cell clusters from tissue having surprisingly superior size, yield and integrity compared to cells or cell clusters isolated using the crude collagenase mixtures of the prior art.

Another aspect of the present invention is the identification of essential components of the purified enzyme mixture as well as preferred ranges and ratios of these essential components for isolating cells or cell clusters from tissue. When the essential components of the purified enzyme mixture are combined in predetermined amounts, the resulting purified enzyme mixture is useful for reproducibly isolating cells or cell clusters from tissue.

More particularly, it has been discovered that, when a crude collagenase composition is purified so that it comprises two collagenase enzymes, two other proteases and only part of the non-protease components originally present in the crude composition, the purified enzyme mixture resulting avoids the problems suffered by the prior art when the purified mixture is used for isolating cells or cell clusters from tissue samples. An especially preferred purified enzyme mixture comprises collagenase I, collagenase II, clostripain and a neutral protease. Preferred neutral proteases are *C. histolyticum* neutral protease, thermolysin, or dispase. Preferred activity ranges are from about 40 to about 270 Wunsch units per pancreatic sample collagenase I, from about 1400 to about 2400 Wunsch units per sample collagenase II, from about 4000 to about 15,000 BAEE units per sample clostripain, and from about 50,000 to about 100,000 FITC-casein units per sample thermolysin. When dispase is used for the neutral protease, the preferred range is from about 50,000 to about 90,000 FITC-casein units per sample. An especially preferred purified enzyme mixture for isolating cells or cell clusters from a porcine or human pancreas comprises about 100 Wunsch units per sample collagenase I, about 1600 Wunsch units per sample collagenase II, about 7,000 BAEE units per sample clostripain, and about 70,000 FITC-casein units per sample thermolysin or dispase.

The term "crude collagenase" as used herein refers to a non-purified mixture containing protease enzymes exhibiting collagenolytic and proteolytic activity as well as non-protease components.

The term "purified enzyme mixture" as used herein refers to a mixture of crude collagenase wherein at least some of the non-protease components have been removed.

Crude Collagenase Purification

It has been discovered in the present invention that when at least some of the non-protease components in a mixture of crude collagenase are removed, the resulting purified enzyme mixture is capable of dissociating tissue with a larger number of cells or cell clusters being recovered than a mixture of crude collagenase possessing the same level of enzyme activities.

Crude collagenase may be obtained from many sources, including mammalian (e.g. human), crustacean (e.g. crab, shrimp), fungal, and bacterial (e.g. from the fermentation of Clostridium, Streptomyces, Pseudomonas, or Vibrio). Collagenase has also been genetically engineered. Any of the above should perform acceptably as a source of crude collagenase. The preferred source of crude collagenase is from a bacterial fermentation process, specifically the fermentation of C. histolyticum. The crude collagenase may be a single crude batch or two or more crude batches mixed together to obtain desired enzyme ratios.

The flowchart below shows a purification process of the present invention.

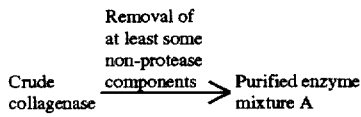

The purification process of the present invention comprises at a minimum the removal of at least some of the non-protease components from the crude collagenase. The resulting mixture (purified enzyme mixture A) exhibits a surprising and marked improvement in performance over the crude collagenase. This removal is preferably accomplished using dye ligand affinity chromatography as described below in Example 1, which removes roughly 85% of the non-protease components from the original collagenase. A measure of the non-protease concentration in a sample can be determined by measuring its absorbance (A) at 280 nanometers (nm) and dividing this value by its absorbance at 360 nm. Non-purified crude collagenase samples have been found to have $A_{280}/A_{360}$ ratios between about 3 and 10, while enzyme samples which have been purified by appropriate dye ligand affinity chromatography have been found to have $A_{280}/A_{360}$ ratios from about 30 to greater than 100.

The removal of at least some of the non-protease components may also be accomplished by various other methods including heparin affinity chromatography (described below in Example 2) and ammonium sulfate precipitation (described below in Example 3). Although the ammonium sulfate precipitation removes only about 25% of the non-protease components, the resulting purified enzyme mixture still displays a significant improvement in performance. Several affinity supports (arginine and benzamidine) were used but were not as effective in separating the non-protease components from the protease enzymes. In addition, other chromatography supports (e.g. propyl, butyl, pentyl, hexyl, heptyl, and octyl omega amino supports, as well as phenyl sepharose hydrophobic interaction supports) were found to separate some of the protease enzymes from the non-protease components, but not as well as the dye ligand supports.

FIG. 1 shows the improvement in performance in pancreatic dissociation when dye ligand affinity chromatography was used on a lot of crude bacterial collagenase obtained from C. histolyticum. The measurement of performance (y-axis) is EIN yield per milligram pancreas, EIN being the "equivalent islet number" which represents the relative islet mass. As is shown in FIG. 1, when a lot of crude collagenase was treated with the above process alone without altering the levels of enzyme activity, the EIN yield was improved from about 4 to more than 9.

The flowchart below shows the preferred purification process of the present invention.

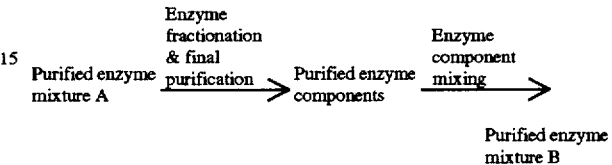

Figure 2:
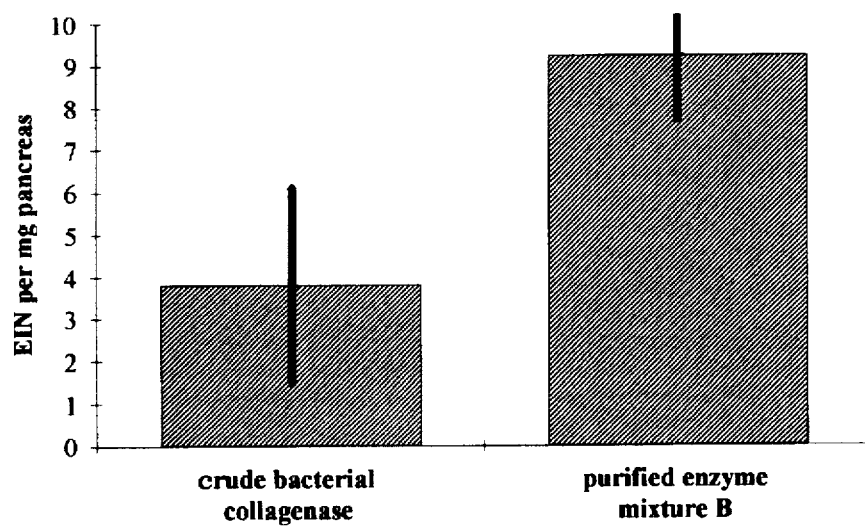
FIG. 2 shows the improvement in performance in pancreatic dissociation after enzyme fractionation and final purification.

As shown above, purified enzyme mixture A may be further purified by fractionation and final purification to yield purified enzyme components, which may then be mixed in known amounts to form purified enzyme mixture B. Examples of enzyme fractionation, final purification, and enzyme component mixing are given below in Examples 4 and 5. FIG. 2 shows the improvement in performance in pancreatic dissociation when the preferred purification process was used on several lots of crude bacterial collagenase obtained from C. histolyticum. As shown in FIG. 2, purified enzyme mixture B exhibits the same marked improvement in performance as purified enzyme mixture A. Because purified enzyme mixture B contains known amounts of the enzyme components, however, its performance is more reproducible. In addition, the ratios of the components of purified enzyme mixture B can be modified, allowing dissociation of different tissue types.

Purified Enzyme Mixture Components

The enzyme mixture of the present invention comprises at least two collagenase enzymes and two other proteases. As discussed above, the collagenase enzymes may be obtained from many sources, including mammalian, crustacean, fungal, and bacterial. Genetically engineered collagenase enzymes may also be used. Preferably, the two collagenase enzymes are collagenase I and collagenase II from C. histolyticum. The two other proteases are preferably clostripain (EC 3.4.24.4) and one or more neutral proteases (e.g. C. histolyticum neutral protease, dispase (EC 3.4.24.4), or thermolysin (EC 3.4.24.4). (EC stands for Enzyme Commission classification. EC 3.4.24.4 is the classification for microbial metalloproteinases.)

Another aspect of the present invention is the identification of the enzyme mass ratios and activity ranges of the two collagenase enzymes and the two other proteases that are preferred for isolating cells or cell clusters from tissue. The preferred mass ratio of collagenase II to the total collagenase in the mixture, collagenase II/(collagenase I+collagenase II), is about 0.3 to about 0.6 and is preferably about 0.4 to 0.45. Example 5 below discloses the preferred enzyme activity ranges for the specific application of isolating islets from pancreas tissue.

EXAMPLE 1

Purification of Crude Bacterial Collagenase by Dye Ligand Affinity Chromatography Commercially available crude bacterial collagenase (collagenase P, Boehringer Mannheim) was used as the starting material. Three dye ligand affinity chromatography supports from Amicon were found to perform acceptably. These supports were MATREX (registered trademark, W. R. Grace & Co.) Gel Blue A, MATREX Gel Red A, and MATREX Gel Green A.

The crude bacterial collagenase and the chosen support were equilibrated against a low ionic strength calcium-containing buffer at a pH between 6.0 to 7.0. For these chromatographies either 20 millimolar (mM) 4-[2-hydroxyethyl]-1-piperazine ethanesulfonic acid (HEPES) or 20 mM [bis-(2-hydroxyethyl)-imino]-tris(hydroxymethyl)-methane (BIS-Tris), 1 mM calcium chloride pH 7.0 buffer were used for binding. The crude bacterial collagenase was dissolved by suspending the lyophilized starting material in the desired buffer at a protein concentration of about 40 milligrams (mg)/milliliter (ml). Particulates were then removed by centrifugation (Sorvall GSA rotor, 10,000 rpm for 30 minutes or equivalent) and/or filtration preferably through a cellulose or cellulose nitrate membrane.

The sample was applied to the resin at a flow rate of 0.5 centimeters (cm)/minute (min). It was found that about 20 mg of collagenase P can be loaded onto each milliliter of MATREX Gel Red A or MATREX Gel Green A support with complete retention of the enzyme activities. Unretained materials were eluted with the equilibration buffer.

The enzyme fractions were recovered using a salt gradient. Elution buffers comprising either (i) 20 mM HEPES, 1 mM calcium chloride, and 400 mM sodium chloride (pH 7.5), or (ii) 20 mM tris-(hydroxymethyl)-aminomethane (Tris), 1 mM calcium chloride, and 150 mM sodium chloride (pH 9.0) were sufficient to recover all of the enzymes.

The purified enzyme mixture A resulting was found to be capable of dissociating tissue in a shorter period of time with a larger number of cells or cell clusters recovered than with the unpurified crude collagenase. The performance of this purified enzyme mixture with a given tissue type (e.g. pancreas), however, will depend on the ratios and concentrations of the enzymes in the crude collagenase used as a starting material. In order to produce a mixture having a known amount of each enzyme present which will reproducibly recover cells or cell clusters from a given tissue type, the enzymes must be separated, further purified, and finally mixed together in the desired concentration (described below in Examples 4 and 5).

EXAMPLE 2

Purification of Crude Bacterial Collagenase by Heparin Affinity Chromatography

Heparin affinity chromatography may also be used to remove at least some of the non-protease components from crude collagenase. Heparin affinity resin from Pharmacia Fine Chemicals was found to perform acceptably. The column and crude bacterial collagenase preparation (e.g. collagenase P) were equilibrated in a low ionic strength neutral buffer containing a calcium salt (10 mM Tris, 5 mM calcium chloride pH 7.4). The sample was applied and washed with buffer until the unretained material was washed from the column. The enzymes were eluted with the same buffer containing sodium chloride (>200 mM).

EXAMPLE 3

Purification of Crude Bacterial Collagenase by Ammonium Sulfate Precipitation

A 60% saturated ammonium sulfate precipitation was also used to remove at least some of the non-protease components from crude collagenase. Crude collagenase (collagenase P) was dissolved at a concentration of 10 to 100 mg/ml in water or low ionic strength neutral buffer. Insoluble material was removed and the enzymes were precipitated by making the solution 60% saturated in ammonium sulfate. This was accomplished by the slow addition of 0.37 grams (g) of solid ammonium sulfate per ml of collagenase solution or by the addition of 1.5 ml of a saturated ammonium sulfate solution per ml of collagenase solution. This process was completed in the temperature range of 2° C. to 8° C. After the complete addition of the ammonium sulfate, the solution was allowed to sit approximately 2 hours to precipitate the desired enzymes. The precipitated enzymes were then recovered.

EXAMPLE 4

Enzyme Fractionation and Final Purification

Enzyme Fractionation

The enriched enzyme pool from the non-protease component removal process in Example 1 above was exchanged into an anion exchange loading buffer. Two buffer systems were used for the fractionation of this enzyme mixture. One used 5 mM HEPES and 1 mM calcium chloride (pH 7.5) as the binding buffer and either diethyl amino ethyl (DEAE) or Q SEPHAROSE Fast Flow support (Pharmacia) for the resin.

After buffer exchange was complete the enzyme solution was clarified and applied to the column at a flow rate of 1 cm/min. On average 20 to 50 mg of protein was loaded per ml of support. The enzymes were eluted with a salt gradient of either 0 to 400 mM sodium chloride or 1 to 100 mM calcium chloride. On average 10 to 15 column volumes of buffer was sufficient for the gradient. Both gradients yielded protein resolution, purity and recovery similar to each other. A total of three enzyme pools were obtained and designated as (i) collagenase II and clostripain, (ii) collagenase I, and (iii) neutral protease.

A variation of the above procedure used a step calcium chloride gradient to elute the enzymes. In this chromatography the clostripain was eluted using 8 mM calcium chloride, the collagenase II pool was eluted with 20 mM calcium chloride, the collagenase I pool was eluted with 35 mM calcium chloride and the neutral protease was eluted with 100 mM calcium chloride. The second buffer system used 20 mM Tris as the buffering agent, pH 9.0, and a step calcium chloride gradient to elute the proteins. The binding buffer contained 1 mM calcium chloride, the collagenase II and clostripain were eluted with 25 mM calcium chloride, the collagenase I was eluted with 35 mM calcium chloride, and the neutral protease was eluted with 100 mM calcium chloride.

Enzyme Final Purification

The collagenase II/clostripain pool was purified by cation exchange chromatography on SP SEPHAROSE Fast Flow ion exchange gel (registered trademark, Pharmacia, Inc.). The resin and the sample were equilibrated against a buffer of 5 mM HEPES and 1 mM calcium chloride (pH 6.5). The sample was applied to an SP SEPHAROSE Fast Flow cation exchange resin at a flow rate of 0.5 cm/min. About 20 to 50 mg of clostripain were applied to each ml of support. After application, the column was washed with loading buffer until the unretained material (collagenase II) was washed from the support. The retained protein components were eluted with either a 0 to 400 mM sodium chloride gradient or a 1 to 100 mM calcium chloride gradient (total gradient was 15 column volumes). The collagenase II was eluted in the unretained fraction, the contaminating proteins were found in an intermediate fraction and the clostripain eluted toward the end of the salt gradient. These two purified enzymes were equilibrated against a buffer of 5 mM HEPES and 1 mM calcium chloride (pH 7.5) and stored frozen at −20° C. at protein concentrations of between 5 mg/ml and 30 mg/ml.

For most production chromatographies the collagenase I pool did not require additional fractionation. Occasionally clostripain or pigment contamination was observed in some pools. On these occasions the collagenase I enzyme was purified by gel permeation chromatography using ACA 44 resin to effect the separation (flow rate 0.25 cm/min). SEPHADEX G-200 and SEPHACRYL S-200 (registered trademarks, Pharmacia, Inc.) resins may also be used to perform the same process. Any buffers containing calcium salts that are compatible with the stability of the enzymes may be used. 20 mM Tris and 1 mM calcium chloride (pH 7.5) or 5 mM HEPES and 1 mM calcium chloride (pH 7.5) both yielded good recovery of mass and activity. Using these supports the collagenase I enzyme was separated from any clostripain or fermentation by-products.

EXAMPLE 5

Preparation of Enzyme Mixtures for the Isolation of Islets from Pancreatic Tissue Purified enzyme mixtures were prepared from the fractionated and purified enzymes by mixing either a specific number of units or specific masses of the enzymes. The specific activities of the collagenase I, collagenase II, and clostripain enzymes were usually consistent enough that both units and mass yielded the same mass ratio of enzymes in the final mixture. Collagenase I, collagenase II, and clostripain were mixed and kept in solution at +4° C. and for longer time periods at −20° C.

Following are three enzyme assays (assays for collagenase, clostripain, and neutral protease) that were used to define the specific activities of the enzyme mixture components as well as the total activity of the enzyme mixture. The specifications and tolerances based on these assays were found to be critical to the performance of the purified enzyme mixture. Those skilled in the art will recognize that enzyme assays other than those disclosed below may also be used.

Collagenase Activity Assay

Collagenase activity was measured using a synthetic peptide substrate according to the method of Wunsch & Heidrich (Z. Physiol Chem. 1963; 333:149). This is a standard method well known to those skilled in the art of collagenase purification. The measured activity of collagenase II (range: 7.5–10.0 units (U)/mg) was approximately 20-fold greater than collagenase I (range: 0.3–0.7 U/mg) using the Wunsch peptide as a substrate. One unit (U) of activity is defined by the hydrolysis of 1 micromole (µmol) peptide per minute at 25° C., pH 7.1.

Clostripain Activity Assay

Clostripain activity was measured by the esterolysis of N-benzoyl-L-arginine ethyl ester (BAEE) according to a modification of the method of Whitaker and Bender (J. Am. Chem. Soc. 1965; 87:2728). Clostripain is a cysteine protease activated by reducing agents such as dithiothreitol (DTT). Measured clostripain activity is the difference between DTT-activated enzyme and non-DTT-treated enzyme. The activities described were generated using 1.8 mM BAEE. The range of measured specific activity for purified clostripain was approximately 70 to 120 U/mg where one unit is defined as the hydrolysis of 1 µmol BAEE per minute at 25° C., pH 7.6. A description of the test procedure used for the clostripain activity assay is given below.

Phosphate Buffer (75 millimole (mmol)/liter (1)):

1.17 g sodium phosphate, monobasic ($NaH_2PO_4$) was dissolved in deionized (DI) water. The volume was adjusted to 100 ml and labeled "solution A". 1.07 g sodium phosphate, dibasic ($Na_2HPO_4$) was dissolved in DI water. The volume was adjusted to 100 ml and labeled "solution B". The pH value of solution B was adjusted to 7.6 with solution A.

DTT Solution (7.5 mmol/l): 28.9 mg dithiothreitol (DTT) was dissolved in DI water and the volume was adjusted to 25 ml.

BAEE Solution (1.8 mmol/l): 15.4 mg BAEE was dissolved in DI water and the volume was adjusted to 25 ml.

10× Activating Solution (10 mmol/l calcium acetate, 25 mmol/l DTT): 17.6 mg calcium acetate and 38.6 mg DTT was dissolved in DI water and the volume was adjusted to 10.0 ml.

10× Blank Solution (10 mmol/l calcium acetate): 17.6 mg calcium acetate was dissolved in RO/DI water and the volume was adjusted to 10.0 ml.

Sample Preparation: 2 mg collagenase P was weighed, reconstituted with 0.9 ml DI water and 0.1 ml 10× Activating Solution, and incubated for 4.5 hours at room temperature. (Before performing the assay, the sample was diluted 10 fold with 1× Activating Solution.)

Trypsin Blank Preparation: Trypsin blanks were prepared by repeating the sample dilutions using 10× Blank Solution in place of 10× Activating Solution and 1× Blank Solution in place of 1× Activating Solution .

Spectrophotometric Assay (wavelength 253 nm. final volume 0.93 ml, temperature 25° C.): A trypsin blank mixture and an activated sample mixture were prepared by mixing the following:

|  | Trypsin blank mixture | Activated sample mixture |
| --- | --- | --- |
| BAEE Substrate | 5.0 ml | 5.0 ml |
| 75 mmol/l phosphate buffer pH 7.6 | 5.0 ml | 5.0 ml |
| DI water | 5.0 ml | — |
| 7.5 mmol/l DTT Solution | — | 5.0 ml |

Four cuvettes were placed in the spectrophotometer. 0.9 ml of the trypsin blank mixture was pipetted to each of the first two cuvettes. 0.9 ml of the activated sample mixture was pipetted to the remaining two cuvettes. The absorbance was read for 1.5 minutes to establish a blank rate (the blank rate should not exceed 0.01 delta $(\Delta)A_{253}$/min). The reaction was then started by pipetting 0.03 ml of the diluted Trypsin Blank Preparation into the two trypsin blank cuvettes and 0.03 ml of the diluted Sample Preparation into the two activated sample cuvettes and mixing thoroughly. Each cuvette was read for 1.5 minutes to determine the reaction rate. (The $\Delta A_{253}$/min should be between 0.007 and 0.040.)

Calculation: For each sample, the U/ml activity was calculated as follows: U/ml=($\Delta$A/minute)×(dilution factor)×(0.93)×(1000)/(1150)×(0.03) where $\Delta$A/minute= $\Delta A_{253}$/min sample−$\Delta A_{253}$/min blank. Simplified, U/ml= ($\Delta$A/minute)×(dilution factor)×(26.92). The U/mg specific activity was calculated for each sample by the following calculation: specific activity (U/mg)=(U/ml)/(mg/ml).

Neutral Protease Activity Assay

Neutral protease activity was measured by the liberation of trichloroacetic acid (TCA) soluble fluorescent peptides from the substrate FITC-casein according to a modified version of the method of Twining (*Anal. Biochem.* 1984; 143:30). Fluorescent peptides were quantified using an excitation wavelength of 491 nm and an emission wavelength of 525 nm. The ranges of measured FITC-casein specific activities for purified neutral proteases were: neutral protease, 200 to 500 U/mg; dispase, 900 to 1300 U/mg; and thermolysin, 2000 to 4500 U/mg. One unit of activity generates 100,000 fluorescent units (counts per second) corrected for background per minute at 37° C., pH 7.5. A description of the test procedure used for the neutral protease activity assay is given below.

Sample Dilution Buffer (100 mmol/l Tris, 10 mmol/L Calcium Chloride ($CaCl_2$), pH 7.5): 6.06 g Tris and 0.74 g $CaCl_2$ were dissolved in DI water. The pH was adjusted to 7.5 with 5N HCl and the volume adjusted to 500 ml.

FITC-Casein Substrate Solution (0.25% w/v): 50.0 mg FITC-casein was dissolved in the Sample Dilution Buffer. The volume was adjusted to 20.0 ml.

Quenching Solution (5.0% w/v): 5.0 g of Trichloroacetic Acid was dissolved in DI water. The volume was adjusted to 100 ml.

Neutralization Solution (500 mmol/L Tris: pH 8.5): 30.3 g Tris was dissolved in DI water. The pH was adjusted to 8.5 with 1N HCl and the volume was adjusted to 500 ml.

Assay Procedure: The samples were diluted with Sample Dilution Buffer to a concentration range of 5 to 50 micrograms (μg)/ml, depending upon estimated sample activity. 10 microliters (μl) of the diluted samples were added to 40 μl of FITC-casein Substrate Solution in a 1.5 ml Eppendorf tube (the Sample Dilution Buffer was used as a blank control) and incubated for 45 minutes with shaking at 37° C. in a water bath. 120 μl of the Quenching Solution was added. The solution stood at room temperature for at least 60 minutes. The solution was then centrifuged at full speed (14,000 rpm) for 2 minutes. 50 μl of the supernatant was removed and added to 2 ml of Neutralization Buffer and mixed by inversion. The sample was decanted to a cuvette and fluorescence was measured (excitation wavelength 491 nm, emission wavelength 525 nm, slit width 0.2 nm).

Calculations: CPS=Average enzyme sample flourescence–Average buffer blank fluorescence. Activity (U/ml)=(CPS×0.17 ml×Dilution factor)/(0.05 ml×0.01 ml×45 min.×100,000). The blank fluorescence should be in a range from 2000 to 3000 CPS using the suggested setting on the SPEX fluorimeter. The linear range for the SPEX fluorimeter is from 2000 to 100,000 CPS.

Figure 3:
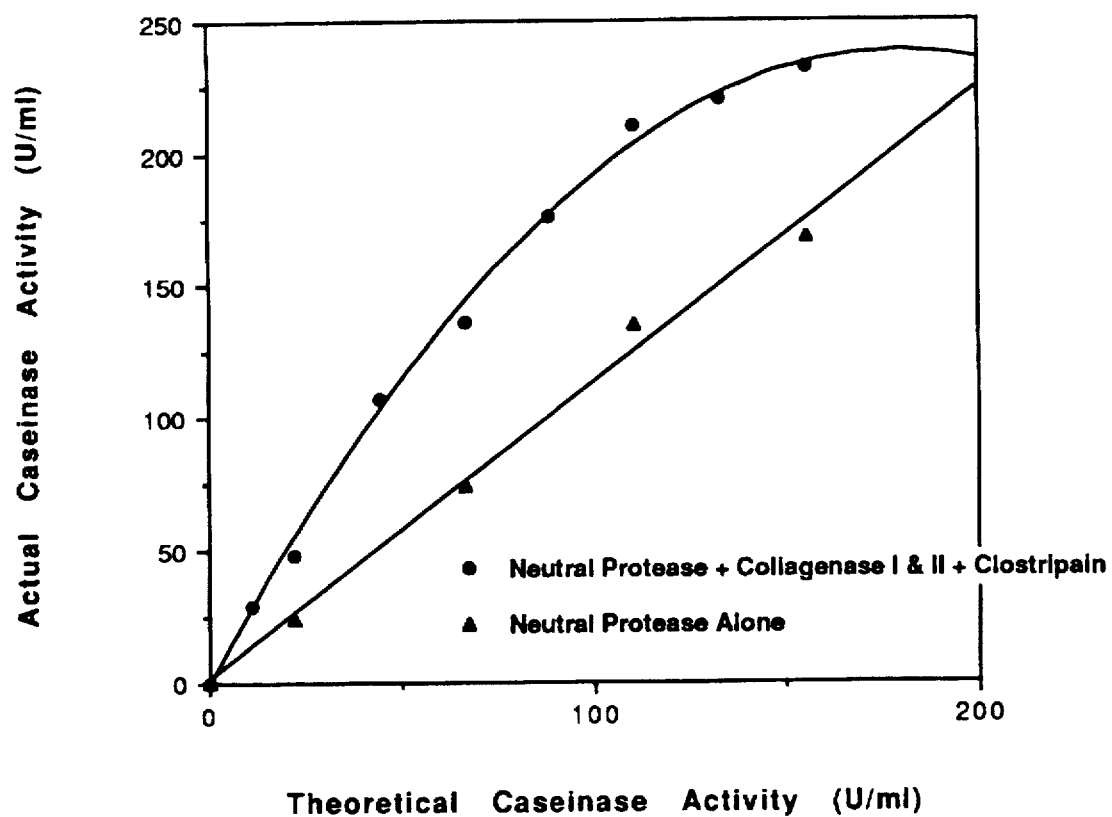
FIG. 3 shows the effect on caseinase activity of neutral protease alone and added to a set ratio of collagenase I, collagenase II, and clostripain.

Importantly, the substrate casein used in the assay for neutral proteases described above can also act as a general substrate for a wide variety of protease activities including trypsin, clostripain, dispase, thermolysin, and many others. As a result, the final units of the added neutral proteases (e.g. thermolysin and dispase in Tables 2 and 3 below) were measured and defined as amplified units in the final enzyme mixture and were not the actual units of the neutral protease components measured alone prior to mixing. An apparent 2- to 3-fold amplification of protease activity has been observed. FIG. 3 and Table 1 below show this amplification effect when *C. histolyticum* neutral protease was used in an FITC-casein assay evaluation of individual and mixed components isolated from collagenase P.

TABLE 1

FITC-casein assay evaluation of individual and mixed components isolated from collagenase P

| Sample Pool* | Caseinase Activity | Theoretical Activity |
|---|---|---|
| neutral protease (NP) | 43.9 U/ml | |
| clostripain (CL) | 16.8 U/ml | |
| collagenase II (CO-II) | 3.3 U/ml | |
| collagenase I (CO-I) | 3.9 U/ml | |
| | 67.9 U/ml (individual total) | |
| NP + CO-I | 49.9 U/ml | 47.2 U/ml |
| NP + CO-II | 61.6 U/ml | 47.8 U/ml |
| NP + CL | 61.2 U/ml | 60.7 U/ml |
| NP + CO-I + CO-II | 90.8 U/ml | 51.1 U/ml |
| NP + CO-I + CO-II + CL | 145.6 U/ml (combined total) | 67.9 U/ml |

*All samples added to assay using equivalent mass based upon $A_{280}$.

The amplification of apparent activity seen in FIG. 3 and above in Table 1 for *C. histolyticum* neutral protease also applies to other neutral proteases (e.g. thermolysin or dispase) added to the enzyme mixture.

The optimal amounts of collagenase I, collagenase II, clostripain, and neutral protease in the purified enzyme mixture will vary depending on the type of tissue to be dissociated. Table 2 below shows the ranges and preferred units and masses for each enzyme component for the dissociation of human pancreas. A typical human pancreatic sample for which the preferred composition has been defined is one weighing approximately 60 to 100 grams and relatively free from congestion (residual blood). Importantly, the upper limits of the activity ranges given for the collagenase I, collagenase II and clostripain enzymes are not critical, i.e., the performance of the purified enzyme mixture does not decrease when the collagenase I, collagenase II and clostripain enzymes are at or above these upper limits.

The specific activities listed in the table are the activities determined for each purified enzyme component. The units range and the preferred units are the measured activities of each component in the final enzyme mixture. For collagenase I, collagenase II, and clostripain, the units range and the preferred units in the final mixture reflect the specific activity of each component times the mass added of the component. For thermolysin, the units range and the preferred units reflect the specific activity of thermolysin times the mass added times an amplification factor as described above.

TABLE 2

Purified Enzyme Mixture For Human Pancreas Dissociation

| Enzyme | Specific Activity | Units Range | Preferred Units | Mass Range | Preferred Mass |
|---|---|---|---|---|---|
| collagenase I | 0.3–0.7 U/mg (Wunsch) | 40–270 U/sample | 100 U/sample | 130–445 mg | 300 mg |

TABLE 2-continued

Purified Enzyme Mixture For Human Pancreas Dissociation

| Enzyme | Specific Activity | Units Range | Preferred Units | Mass Range | Preferred Mass |
| --- | --- | --- | --- | --- | --- |
| collagenase II | 7.5–10.0 U/mg (Wunsch) | 1,400–2,400 U/sample | 1600 U/sample | 150–240 mg | 200 mg |
| clostripain | 70–120 U/mg (BAEE) | 4,000–15,000 U/sample | 7,000 U/sample | 30–190 mg | 60 mg |
| thermolysin | 2000–4500 U/mg (FITC-casein) | 50,000–100,000 U/sample | 70,000 U/sample | 7–10 mg | 7 mg |

After enzyme fractionation and final purification of the collagenase I, collagenase II, and clostripain enzymes as described above, the proteins were concentrated to 10–25 mg/ml. The enzymes were then buffer exchanged into a 5 mM HEPES, 1 mM $CaCl_2$ (pH 7.5) buffer, and the specific activity of each enzyme was determined. The desired amounts of collagenase I, collagenase II, and clostripain enzymes were then gently mixed to form a homogeneous solution. If the tissue dissociation was to be done the same day, this solution was kept on ice at +4° C. until needed. The desired amount of thermolysin was then dissolved in 1 to 2 ml water or buffer and gently mixed until completely dissolved. The thermolysin solution was then added to the collagenase I, collagenase II, and clostripain solution and mixed until uniform. This purified enzyme mixture was then diluted as desired for the dissociation of the pancreas.

Table 3 below shows the ranges and preferred units and masses for each enzyme component for the dissociation of porcine pancreas. A typical porcine pancreatic sample for which the preferred composition has been defined is one weighing approximately 60 to 100 grams and relatively free from congestion (residual blood).

EXAMPLE 6:

Protocol for Porcine Pancreas Dissociation

Following is an example of how the purified enzyme mixture of the present invention was used to dissociate a porcine pancreas and recover viable islet cells. The same procedure was also used for human islet isolation.

Dissociation System Set Up

Figure 4:
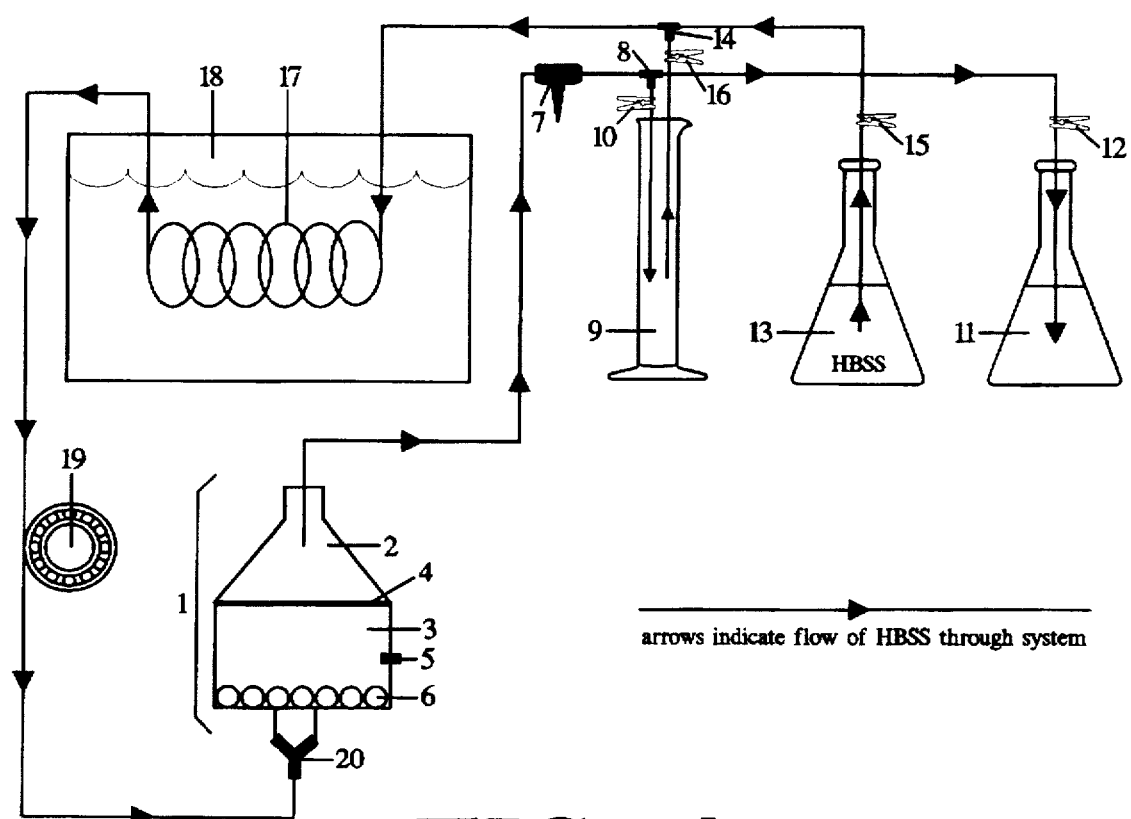
FIG. 4 shows a tissue dissociation system that can be used in the practice of the present invention.

A dissociation system that was used in accordance with the present invention is shown in FIG. 4. Ricordi 500 ml dissociation chamber 1 (C. Ricordi, Diabetes Research Institute, University of Miami, Fla.) included upper portion 2, lower portion 3, wire mesh screen 4 (400 micrometer (μm) pore size×3.75 inch (") diameter), Mon-a-therm Model 6510 temperature sensor 5, and seven (7) 1 cm diameter glass marbles 6.

Chamber 1 was connected to stopcock 7 by silicone tubing. Stopcock 7 was connected to T-connector 8 by silicone tubing. T-connector 8 was connected to 100 ml graduated cylinder 9 by silicone tubing. Clamp 10 was located along the tubing between T-connector 8 and cylinder 9. T-connector 8 was also connected to collection vessel 11

TABLE 3

Purified Enzyme Mixture For Porcine Pancreas Dissociation

| Enzyme | Specific Activity | Units Range | Preferred Units | Mass Range | Preferred Mass |
| --- | --- | --- | --- | --- | --- |
| collagenase I | 0.3–0.7 U/mg (Wunsch) | 40–270 U/sample | 100 U/sample | 130–445 mg | 300 mg |
| collagenase II | 7.5–10.0 U/mg (Wunsch) | 1,400–2,400 U/sample | 1600 U/sample | 150–240 mg | 200 mg |
| clostripain | 70–120 U/mg (BAEE) | 4,000–15,000 U/sample | 7,000 U/sample | 30–190 mg | 60 mg |
| dispase | 900–1300 U/mg (FITC-casein) | 50,000–90,000 U/sample | 70,000 U/sample | 50–80 mg | 80 mg |

The purified enzyme mixture for porcine pancreas dissociation was prepared as described above for the human pancreas dissociation mixture, except dispase was used in place of thermolysin.

The purified enzyme mixtures described above for human and porcine pancreas dissociation are expected to perform acceptably for other tissue types as well. As will be apparent to those skilled in the art, some modification may be necessary to optimize the purified enzyme mixture for dissociating specific tissue types, e.g. tissues which contain more collagen may require increased collagenase activity and tissues which contain more non-collagen proteins may require increased protease activity. Similarly, pancreatic tissue samples smaller or larger than 60 to 100 grams might necessitate corresponding adjustments in enzyme activity.

(1-liter Erlenmeyer flask) by silicone tubing. Clamp 12 was located along the tubing between T-connector 8 and collection vessel 11.

Addition vessel 13 (1-liter Erlenmeyer flask) was connected to T-connector 14 by silicone tubing. Clamp 15 was located along the tubing between addition vessel 13 and T-connector 14. Addition vessel 13 contained Hanks Balanced Salt Solution (HBSS), described below. The arrows in FIG. 4 indicate the flow of HBSS through the system. T-connector 14 was connected to cylinder 9 by silicone tubing. Clamp 16 was located along the tubing between T-connector 14 and cylinder 9.

T-connector 14 was also connected to a first end of stainless steel coil 17 (coil length=80") in water bath 18 (Lauda M20, Biodynamics) by tubing. The second end of stainless steel coil 17 was connected to Y-connector 20 by tubing. Master Flex pump 19 (Cole Palmer) was located along the tubing between stainless steel coil 17 and Y-connector 20. Y-connector 20 was connected to lower portion 3 of chamber 1 by two pieces of tubing. (Note: only 2 of clamps 10, 12, 15, 16, and were in use at any given time.)

Dissociation Solution Preparation

FBS: Fetal Bovine Serum (FBS) (HyClone, heat inactivated) was thawed to room temperature and placed in a 56° C. water bath for 30 minutes, swirled periodically, and stored at 4° C.

Stock Ficoll Buffer: 1 L of Eurocollins solution (Fresenius) was prepared and emptied into a 1 L flask. 500 g Ficoll 400DL Molecular Grade (Sigma) was weighed in a 4 L beaker with a stir bar. The 1 L Eurocollins solution was slowly added (500 ml/10 min). 8.94 g HEPES (Boehringer Mannheim) was added. The mixture was covered with PARAFILM (registered trademark, American National Can Co.) moisture-proof wrapper and stirred overnight. The next day, the solution pH was brought to 7.40 with 10N NaOH (Mallinckrodt). The solution was then sterilized by autoclaving at 100° C. for 15 minutes, then stored at 4° C.

Ficoll Buffer/Eurocollins solution gradient: Four solutions were prepared with stock Ficoll buffer densities of 1.125 g/cm$^{-3}$, 1.080 g/cm$^{-3}$, 1.060 g/cm$^{-3}$, and 1.037 g/cm$^{-3}$ (stock Ficoll buffer density was 1.134 g/cm$^{-3}$), using Eurocollins solution as the diluent. For the 1.125 g/cm$^{-3}$ solution, 900 ml stock Ficoll buffer was added to 140 ml Eurocollins solution. For the 1.080 g/cm$^{-3}$ solution, 500 ml of the 1.125 g/cm$^{-3}$ solution was added to 320 ml Eurocollins solution. For the 1.060 g/cm$^{-3}$ solution, 400 ml of the 1.080 g/cm$^{-3}$ solution was added to 200 ml Eurocollins solution. For the 1.037 g/cm$^{-3}$ solution, 160 ml of the 1.060 g/cm$^{-3}$ solution was added to 190 ml Eurocollins solution. The density was checked after each dilution (target density+/−0.002 g/cm$^{-3}$) and adjusted if necessary using a PAAR DMA 35 density meter (AntonPaar USA, Inc.).

Culture Media: 500 ml sterile water was autoclaved at 121° C. for 30 minutes. FUNGIZONE Amphotericin B antibiotic (registered trademark, E. R. Squibb & Sons, Inc.) (Gibco) was reconstituted with 20 ml of the sterile waters 1 ml of the reconstituted FUNGIZONE, 500 microliters (µl) Pen-Strep (10,000 U P, 10,000 µg S) (Gibco), and 50 ml FBS were added to 500 ml CMRL 1066 (Gibco).

Quenching Buffer: 100 ml FBS was added to 900 ml Hanks Balanced Salt Solution (HBSS) (Sigma).

Stock DTZ Solution: 200 mg Dithizone (DTZ) (Sigma) was added to 80 ml Dimethylsulfoxide (DMSO), swirled to mix, and allowed to equilibrate.

Working DTZ Solution: 80 ml stock DTZ solution was added to 720 ml HBSS and swirled to mix. The solution was divided into 50 ml conical tubes (40 ml each) and stored at −20° C. until used.

Working Collagenase Solution: Just prior to perfusing the pancreas, 1 L HBSS was warmed to 28°–32° C. in a water bath. 200 mg DNase I (Boehringer Mannheim) was added. 667 ml minus the liquid enzyme volume HBSS/DNase was removed and transferred to a glass bottle. The liquid equivalent of 1.0 g of the purified enzyme mixture (described above in Example 5 and Table 3) was added and swirled to mix (final volume=667 ml). The solution was then sterile filtered using a Corning 0.2 µm CA filter unit. The working collagenase solution was maintained at 28°–32° C., with warming as necessary in a water bath.

Surgical Removal of Pancreas

Preparation: Prior to obtaining the Pancreas, the working DTZ solution, quenching buffer, and culture media were warmed to room temperature. Water bath 18 was turned on and set to 45° C. HBSS was added to the dissociation system by applying clamps 12 and 16. Once the HBSS level reached 100 ml in cylinder 9, clamp 16 was removed and clamp 15 applied. HBSS was circulated to warm the dissociation system. 1 L HBSS was placed in another water bath and set to 30° C.

Procurement: The time from stunning the pig (shooting or stunning gun) to exsanguination was noted. Once the pig was exsanguinated, the abdomen was swabbed with iodine solution and opened with a sterile scalpel. The intestines were retracted and stomach lifted using lap sponges. The splenic lobe of the pancreas was removed using blunt dissection. The portal vein was cut last. The pancreas was placed in 300 ml pre-chilled Eurocollins solution (on ice). The warm ischemia time was noted (time from exsanguination to placement of gland in pre-chilled Eurocollins solution). The timer was restarted for the cold ischemia time (time for transporting, cleaning, perfusing, and placing gland in dissociation chamber). The weight and sex of the pig were noted.

Dissection and Perfusion of Pancreas

DTZ was put into a 60 cc syringe with a 0.2 µm filter tip. The pancreas was rinsed with HBSS and placed in a small tray on ice. The fat was removed using blunt dissection. The neck was cannulated by locating the duct, inserting a cannula catheter, adding a needle, tying off the cannula catheter with suture, and removing the needle. The cleaned and cannulated pancreas was weighed. The lobe was then perfused by filling the gland with 180–240 ml of the working collagenase solution using a 60 cc syringe. The gland was lifted as it was perfused. The volume of collagenase added was noted. Leaks were clamped and the neck was clamped after removing the cannula.

Dissociation of Pancreas

Dissociation: The dissociation system was emptied by applying clamp 10 and releasing clamp 12 and the circulation buffer was collected in a 1 L bottle. The perfused pancreas was placed into lower portion 3 of dissociation chamber 1 with marbles 6. Excess (warmed) working collagenase solution was added (as little of the blood-contaminated collagenase (from the pan) was added as possible). Wire mesh screen 4 was placed over lower portion 3 of dissociation chamber 1 and upper portion 2 of dissociation chamber 1 on top of lower portion 3. The dissociation system was filled with working collagenase solution from addition vessel 13 by applying clamps 12 and 16. Once the collagenase solution reached 100 ml in cylinder 9, clamp 16 was removed and clamp 15 was applied. A closed circulation system was thus established. The cold ischemia time was noted (the time from when the pancreas was put in Eurocollins solution until the pancreas was put into dissociation chamber 1 and circulation began). The timer was restarted for the dissociation time. Pump 19 speed was adjusted to 85 ml/min. Chamber 1 was gently rocked by hand (but not inverted). Chamber 1 was shaken once per minute starting at 5 minutes into the dissociation. Once dissociation chamber 1 reached 37° C., water bath 13 temperature was set to 40.5° C. and adjusted with ice. The dissociation time was noted.

Sampling: The circulating solution was inspected by placing DTZ in a 35 millimeter (mm) Costar petri dish, collecting about 1 ml of the circulating solution from stopcock 7, and looking at the solution under a microscope for free islets. Dissociation was stopped when >60% islets were free (small fragmented islets were not seen and exocrine tissue began to look "loose"). 2 ml of the circulating solution was then collected from stopcock 7 in a 15 ml conical tube. 150 µl was removed for counting, placed in a 35 mm petri dish with DTZ, and viewed under a light microscope (100× magnification, 10× eyepiece, 10× objective). Islet counts were correlated to EIN using the conversion method of Ricordi ("Pancreatic Islet Cell Transplantation", C. Ricordi MD, 1992, R. G. Landes Company, page 133). The volume remaining in cylinder 9 was noted after dissociation to back calculate dilution factors (667 ml starting volume was assumed). 2 ml of the circulating solution was collected from stopcock 7 in a 4.5 ml Nalgene tube and stored on ice for an enzyme assay.

Collection: Quenching buffer was added to the dissociation system for dilution by removing clamps 12 and 15 and applying clamps 10 and 16. The flow rate of pump 19 was increased to 160 ml/min. Stainless steel coil 17 was removed from water bath 18. Chamber 1 was rocked gently by hand. 500 ml quenching buffer was placed into two 1 L centrifuge bottles. Cylinder 9 was emptied into the first 1 L bottle. Six liters were collected and spun in a Beckman centrifuge (rotor JS4.2) at 284×G (1000 rpm), 3 minutes, without brake. The brake was applied only at vibrational frequency (about 600 rpm). The supernatants were aspirated leaving about 150 ml in each bottle. The pellets were resuspended by swirling and combining pellets from all bottles. The pellet was then washed with 1 L quenching buffer and spun at 284×G (1000 rpm), 3 min., without brake (except at about 600 rpm). The supernatant was aspirated. The pellet was resuspended by swirling and gentle trituration. Quenching buffer was added to total volume 150 ml (pre-Ficoll count). The solution was then divided into 50 ml conical tubes and spun in a Sorvall centrifuge RT600B 400×G (1400 rpm), 3 min., without brake. The supernatants were aspirated. The pellet was resuspended in Eurocollins solution for a final volume of 70 ml.

Gradient Purification: The gradient components were warmed at room temperature 10 minutes prior to use. The gradients were bottom loaded and layered in 150 ml glass round bottom conical tubes (7.7 ml cell suspension+42.3 ml 1.125, 25 ml 1.080, 25 ml 1.060, 25 ml 1.037). The tubes were spun in a Beckman centrifuge (rotor JS4.2) 400×G (1200 rpm) at 10° C. for 25 minutes, no brake. (Pool interfaces: interface 1—1.037/1.060, interface 2—1.060/1.080, interface 3—1.080/1.125) The layers were washed twice by bringing the total volume to 250 ml with quenching buffer, spinning in a Sorvall centrifuge (RT600B), 400×G (1200 rpm) at 10° for 10 minutes without brake, aspirating the supernatant, and resuspending the pellet and repeating for a second wash or resuspending the pellet in 10 ml culture media. Each layer was looked at and counted if warranted (post Ficoll count).

The above apparatus and protocol serve as an example of how dissociation using the purified enzyme mixture of the present invention may be carried out. It will be apparent to those skilled in the art that other methods may be used in accordance with the present invention to perform the dissociation.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

What is claimed is:

1. An enzyme composition prepared by combining defined amounts of proteases said composition comprising collagenase I and collagenase II from C. histolyticum, having an $A_{280}/A_{360}$ ratio of greater than 30 and two other proteases, wherein the ratio of the mass of collagenase II to the mass of collagenase I plus the mass of the collagenase II in the composition is about 0.3 to about 0.6.

2. The composition of claim 4 wherein the ratio of the mass of collagenase II to the mass of collagenase I plus the mass of collagenase II is about 0.4 to about 0.45.

3. The composition of claim 1 wherein the collagenase I and collagenase II have an $A_{280}/A_{360}$ ratio greater than 100.

4. The enzyme composition of claim 1 wherein at least one of the two other proteases is a neutral protease.

5. The enzyme position of claim 4 wherein the neutral protease is selected from the group consisting of thermolysin, dispase and C. histolyticun neutral protease.

6. The composition of claim 5 wherein the ratio of the mass of collagenase II to the mass of collagenase I plus the mass of collagenase II is about 0.4 to about 0.45.

7. The enzyme composition of claim 4 wherein the neutral protease is thermolysin.

8. The enzyme composition of claim 7 wherein the ratio of the total FITC casein activity of the enzyme composition to the total Wunsch units of activity of the masses of collagenase I and collagenase II in the composition is about 19:1 to about 70:1.

9. The enzyme composition of claim 4 wherein the neutral protease is dispase.

10. The enzyme composition of claim 9 wherein the ratio of the total FITC casein activity of the enzyme composition to the total Wunsch units of activity of the masses of collagenase I and collagenase II in the composition is about 19:1 to about 62:1.

11. The enzyme composition of claim 4 wherein the neutral protease is dispase or thermolysin and the ratio of total FITC casein activity of the enzyme composition to the total Wunsch units of the masses of collagenase I and collagenase II in the composition is about 41:1.

12. The enzyme composition of claim 4 wherein the two other proteases are a neutral protease and clostripain.

13. The enzyme composition of claim 12 wherein the neutral protease is selected from the group consisting of thermolysin, dispase and C. histolyticum neutral protease.

14. The enzyme composition of claim 12 wherein the neutral protease is thermolysin.

15. The enzyme composition of claim 14 wherein the ratio of the total FITC casein activity of the enzyme composition to the total Wunsch units of activity of the masses of collagenase I and collagenase II in the composition is about 19:1 to about 70:1.

16. The enzyme composition of claim 12 wherein the neutral protease is dispase.

17. The enzyme composition of claim 16 wherein the ratio of the total FITC casein activity of the enzyme composition to the total Wunsch units of activity of the masses of collagenase I and collagenase II in the composition is about 19:1 to about 62:1.

18. The enzyme composition of claim 12 wherein the neutral protease is dispase or thermolysin and the ratio of total FITC casein activity of the enzyme composition to the total Wunsch units of the masses collagenase I and collagenase II in the composition is about 41:1.

19. The composition of claim 12 wherein the ratio of the mass of collagenase II to the mass of collagenase I plus the mass of collagenase II is about 0.4 to about 0.45.

20. A method of preparing an enzyme composition adapted for isolating living cells from tissue, said method comprising the steps of combining collagenase I, collagenase II, and clostripain from C. histolyticum wherein the ratio of the mass of collagenase II to the mass of collagenase I plus the mass of collagenase II is about 0.3 to about 0.6; and adding an amount of a neutral protease sufficient to raise the total FITC casein activity of the enzyme composition to a level such that the ratio of the total FITC casein activity of the enzyme composition to the total Wunsch unit activity of the masses of collagenase I and collagenase II in the enzyme composition is about 19:1 to about 70:1.

21. The method of claim 20 wherein the ratio of the mass of collagenase II to the mass of collagenase I plus the mass of collagenase II is about 0.4 to about 0.45.

* * * * *